US006930224B1

(12) United States Patent
Larkin et al.

(10) Patent No.: US 6,930,224 B1
(45) Date of Patent: Aug. 16, 2005

(54) **METHODS FOR PLANT TRANSFORMATION AND REGENERATION OF *PAPAVER SOMNIFERUM***

(76) Inventors: Philip J. Larkin, 82 McInnes Street, Weston, ACT 2601 (AU); Julie Anne Chitty, 35 Gillespie Street, Weetangera, ACT 2614 (AU); Richard Ian Scott Brettell, 8 Weston Street, Yarralumla, ACT 2600 (AU)

( * ) Notice: Subject to any disclaimer, the term of this patent is extended or adjusted under 35 U.S.C. 154(b) by 0 days.

(21) Appl. No.: 09/600,025

(22) PCT Filed: Jan. 7, 1999

(86) PCT No.: PCT/AU99/00004

§ 371 (c)(1),
(2), (4) Date: Aug. 29, 2000

(87) PCT Pub. No.: WO99/34663

PCT Pub. Date: Jul. 15, 1999

(30) Foreign Application Priority Data

Jan. 8, 1998 (AU) ..................................... PP1258
Jan. 9, 1998 (AU) ..................................... PP1280

(51) Int. Cl.$^7$ ........................... C12N 5/04; C12N 15/82
(52) U.S. Cl. ...................... 800/278; 435/430; 800/279; 800/293; 800/294
(58) Field of Search ............................. 435/430, 430.1, 435/419, 418, 417, 470, 469, 320.1; 800/278, 800/279, 289, 290, 294, 293, 298, 323, 300

(56) References Cited

U.S. PATENT DOCUMENTS 5,932,782 A * 8/1999 Bidney ....................... 800/296

OTHER PUBLICATIONS

Yoshimatsu et al., 11.9 Genetic Transformation in *Papaver somniferum L.* ( Opium Poppy) for Enhanced Production of Morphinan, 1996, Biotechnology in Agiculture and Forcearty, vol. 38, pp. 243-252.*
Hansen et al., Recent advances in the transformation of plants, Jun. 1999, Trends in plant science, vol. 4, No. 6, pp. 226-230.*
Block, Factors Influencing the Tissue Culture and the Agrobacterium tumefaciens-Mediated Transformation of Hybrid Aspen anc Poplar Clones, 1990, Plant Physol, vol. 93, pp. 1110-1116.*
Park et al 2002, Antisense RNA-mediated suppression of benzophenanthridine alkaloid biosynthesis in transgenic cell cultures of California poppy. Plant Physiology 128:696-706.*
Wetherell 1982, Introduction to In Vitro Propagation, Avery Publishing Group Inc. Wayne, New Jersey, pp. 27, 40 and 46.*

Li, X. (et al.) 1997 "Factors Affecting Transformation of Efficiency of Poplar Hybrid Line NC5331 by Agrobacterium Tumefaciens" Journal of Arkansas Academy of Sciences, vol. 51, pp116-120.
Williams, R.D., and Ellis, B.E. (1993) "Alkaloids from Agrobacterium Rhizogenes-transformed *Papaver somniferum* cultures". Phylochemistry vol. 32, No. 3, pp. 719-723.
Belny. M., Herouart, D. Thomasset, B. David, H., Jacquin-Dubreuil, A., and David, A. (1997). Transformation of *Papaver somniferum* cell Suspension cultures with sam 1 from *A. thaliana* results in cell lines of different S-adenosyl-L-methionine synthase activity. Physiol Plant. 99:233-240.
Fenning TM, Tymens SS. Brasier CM Gartland JS. Gartland KMA Ahuja MR Boerjan W. and Neale DB 1996. A strategy for the genetic manipulation of English elm. IN "Somatic cell genetics and molecular genetics of trees". pp 105-112 Kluwer Academic Publishers. Dordrecht, Netherlands.
Fenning TM Tymens SS Gartland JS Brasier CM and Gartland KMA. 1996 Transformation and regeneration of English elm using wild-type *Agrobacterium tumefaciens*. Plant Science (Limerick) 116:p37-46.
Galvez L., and R.B. Clark, 1991. Nitrate and Ammonium Uptake and Solution pH Changes for Al-Tolerant and Al-Sensitive Sorghum (Sorghum biocolor) Genotypes Grown and Without Aluminium. Plant and Soil 134:179-88.
Holdford P, Hernandez N, and Newbury HJ. 1992, Factors influencing the efficiency of T-DNA transfer during co-cultivationof Antirrhinum majus with *Agrobacterium tumefaciens*. Plant Cell Reports 11:196-99.
Ikuta A, Syono K, and Furuya T (1974) Alkaloids of callus tissues and redifferentiated plantlets in the Papaveraceae, Phytochemistry 13:2175-2179.
Ilahi I. (1982). Tissue culture of opium poppy cotyledons. In: Plant Tissue Culture 1982. Tokyo, Japan Japanese Association for Plant Tissue Culture.pp81-82.
Ilahi, I and Jabeen, M. (1987). Callus and Plantlet induction in *Papaver somniferum*, Acta Horticulturae 212:697-699.
Li WB, and Komatsuda T. 1995. Impact of several factors related to inoculum, explants, compound and growth medium on tumorigenesis in vitro culture of soybean (Glycine gracilis and G. Max). Soybean Geneticsw Newsletter 22:p93-98.
Nessler CL (1982). Somatic embryogenesis in the opium poppy, *Papaver Somniferum*. Physiologia Plantarum 55: p453-458.
Nessler CL and Mahlberg PG (1970). Ultrastructure of laticifers in redifferentiated organs on callus from *Papaver somniferum* (Papaveraceae). Canadian Journal of Botany 57:675-685.

(Continued)

Primary Examiner—David H Kruse

(57) ABSTRACT

The present invention is concerned with methods of producing transgenic plants, in particular poppy plants, by way of transfecting and/or regenerating plant material under specified culture conditions which prevent, reduce the rate of or delay the rise in pH of the culture medium.

14 Claims, 8 Drawing Sheets

OTHER PUBLICATIONS

Nessler, C.L. (1990). poppy. In Handbook of Plant Tissue Culture. Ornamental Species. Vol 5' (D.A. Evan, W. M. Sharp, and P.V. Ammirato, Eds.). pp 693-713, MacMillan Publishing Co.

Nietz, R. P. 1994. Growth of embryogenic sweet orange callus on media varying in the ratio of nitrate to ammonium nitrogen. Plant Cell Tissue and Organ Culture 39:1-5.

Schmitz: U., and H. Lorz. 1990 Nutrient Uptake in Suspension Cultures of Graminee 2. Suspension Cultures of Rice (Oryza Sativa L). Plant Science 66:95-111.

Schuchmann R and Wellmann E (1983). Somatic embryogenesis of tissue cultures of *Papaver somniferum* and Papaver orientale and its relationship to alkaloid and lipid metabolism. Plant Cell Reports 2:88-91.

Smith, D. L. and A.D. Krikorian, 1990. Somatic Embryogenesis of Carrot in Hormone-Free Medium-External pH Control over Morphogenesis. American Journal of Botany 77:1634-47.

Wakhlu AK and Bajwa PS (1986). Regeneration of uniform plants form somatic embryos of *Papaver somniferum* (opium poppy). Phytomorphology 36:p101-105.

Yoshikawa T and Furuya T (1983). Regeneration and in vitro flowering of plants derived from callus cultures of opium poppy (*Papaver somniferum*). Experientia 39:1031-1033.

Yosimatsu, K. and Shimomura, K. Transformation of opium poppy (*Papaver somniferum* 1) with Agrobacterium rhizogenes MAFF—03-01724. Plant Cell Reports 11, 132-136. Apr. 1992.

* cited by examiner

A

B

C

1. Tobacco + control pBSF16

2. Poppy - control

3. C58: 45-25-2

4. Norman: 48-1

5. Norman: 48-3

6. C58: 45-25-4

7. C58: 45-25-7

8. C58: 45-25-9

9. Tobacco + control pBSF16

10. Poppy – control C58

US 6,930,224 B1

METHODS FOR PLANT TRANSFORMATION AND REGENERATION OF *PAPAVER SOMNIFERUM*

CROSS-REFERENCE TO RELATED APPLICATIONS

This application is the national stage filing under 35 U.S.C. § 371 of International Application No. PCT/AU99/00004 filed Jan. 7, 1999 and published Jul. 15, 2001 as International Publication No. WO 99/34663 which in turn claims benefit under 35 U.S.C. § 119 of Australian Application Number PP1258 filed Jan. 8, 1998 and Australian Patent Application Number PP1280 filed Jan. 9, 1998.

TECHNICAL FIELD

The invention relates to methods for the genetic transformation of plants and methods for regeneration of transgenic plants. In particular the invention relates to methods of transformation and/or regeneration of transgenic poppy plants.

BACKGROUND ART

The importance of the plants of the poppy family, for example *Papaver* and *Eschscholtzia* species, as a commercial source of medicinal opiates and related compounds is well known, and requires little introduction. The demand for these plant products is high.

Suitable agricultural land for commercial poppy growing is limited. Poppies need fertile, free draining soil which is not overly acidic. To reduce the build up of disease in commercially grown poppies, crops must be grown with at least a three year rotation (e.g. at least two to three different crops should be grown in the soil before poppies are grown again). There are other limitations such as topography and availability of water for irrigation. Presently in some areas, the crop area is probably close to the sustainable level—if higher yield of poppy products are desired then it will be necessary to either shorten the rotation or expand the area under cultivation to include marginal soil types. It is expected that employing these less than desirable practices will impact on factors such as yield and quality and produce undesirable related outcomes such as soil erosion and so on.

The alkaloid content in harvested poppy straw in Tasmania, for example, is generally in the range of 1.2% to 2.7% on a dry weight basis. The financial return to the growers is calculated on the basis of the alkaloid content. Thus, high alkaloid content plants mean that the poppy industry can compete with alternative crops which might potentially be grown in the same soils. High alkaloid content in the poppy crops makes the whole industry more competitive. Fewer hectares of crops would need to be grown to produce the same amount of alkaloid, and costs associated with harvesting, transport, storage, extraction and waste disposal would be reduced. Thus, high alkaloid producing poppies are highly desirable to growers, pharmaceutical companies and consumers of refined poppy products.

Conventional plant breeding has produced significant advances in poppy alkaloid contents over the last two decades. However, it appears that the amount of additional improvement possible through conventional breeding is limited.

Genetic transformation of poppies offers the opportunity to improve the alkaloid content of poppy crops and poppy straw. This could occur through a number of ways, including:

enhancement of activity of enzymes at "bottlenecks" in the alkaloid synthetic pathway;

blockage of undesirable "side reactions"; and blockage of the synthetic pathway so that certain desirable alkaloids accumulate (e.g. thebaine, codeine, oripavine etc.).

These types of improvement would thus allow the industry to continue to expand without increasing the area of crops grown. They would also introduce efficiencies throughout the production process.

As well as increasing the yield of desirable plant products, it is desirable to use related biotechnological procedures to introduce herbicide resistance into poppies. At present herbicide control of weeds in poppy crops is difficult and costly. Herbicides are not developed specifically for poppies and the spectrum of weed control of any one herbicide is not very wide. Thus programs of herbicides are applied involving a number of different products tank-mixed and applied in sequence. Development of a herbicide resistant poppy will enable the use of a herbicide with a wider margin of crop safety, and a wider weed spectrum than currently available. The cost of such weed control is expected to be significantly less than presently involved.

Genetic transformation may also be used to introduce other genes into poppies to impart commercially desirable properties, for example, resistance to disease, resistance to acid soil and resistance to insects and other pests.

Despite the desirability of such transformations, it has so far proved difficult to produce viable transgenic poppies. Attempts using conventional methods to introduce specific gene sequences encoding for certain properties and subsequent regeneration of transgenic poppies with predictable properties have thus far been mostly unsuccessful.

Thus there exists a need to develop methods for stably introducing genetic material into a plant which results in a plant which is viable and which possesses the desired traits.

It is an object of the present invention to overcome or ameliorate at least one or more of the abovementioned deficiencies in the prior art, or provide a useful alternative.

SUMMARY OF THE INVENTION

The present applicant has found that there is an unexpected and rapid rise in the pH of the culture medium when plant cells, such as poppy cells, are cultured. This rise in pH is observed around poppy cultures including initial explants (eg. seedling hypocotyls), undifferentiated callus, and callus regenerating via somatic embryos or shoots. This feature of plant cultures, such as poppy cultures, is at least in part responsible for lack of success in regenerating poppy plants and recovering transgenic poppy plants.

Throughout this specification, "type I callus" is translucent callus which can be colourless or brown, and is composed of large vacuolate cells. "Type II callus" is white to brownish opaque callus, composed of small cytoplasmic cells and having the capacity to form somatic embryos and meristemoids.

The term "pH measurements" in the context of the present specification refers to pH measurements taken using a strip of agar from the medium in which the cultured tissue is growing, homogenising in water and reading the pH by conventional means. It will be clear to those skilled in the art that changes of pH in the immediate microenvironment of the plant tissue or cells may be more extreme than those measured at some distance (usually 1 cm) from the cells.

According to a first aspect, the invention provides a method of producing a transgenic plant comprising the steps of:

1) introducing exogenous genetic material into plant material in the presence of a buffering agent which prevents, reduces the rate of or delays the rise in pH of culture medium or plant material.
2) culturing said plant material in the presence of a buffering agent which prevents, reduces or delays the rate of rise in pH of the culture medium or plant material; and
3) regenerating a transgenic plant from said plant material.

According to a second aspect, the invention provides a method of transforming a plant comprising the step of introducing exogenous genetic material into plant material in the presence of a buffering agent which prevents, reduces the rate of or delays the rise in pH of culture medium or plant material.

According to a third aspect, the invention provides a method of producing a transgenic plant from plant material harbouring exogenous genetic material comprising the steps of:

1) culturing said plant material in the presence of a buffering agent which prevents, reduces the rate of or delays the rise in pH of the culture medium or plant material; and
2) regenerating a transgenic plant.

Preferably the plant is an alkaloid producing poppy plant and even more preferably the plant is selected from the *Papaver* species or *Eschscholtzia* species. The most preferred species is *Papaver somniferum*.

Preferably the plant material is derived from seeds, imbibed seeds or seedling parts of the plant. Preferably the plant material is selected from the group comprising seed explant, seedling explant, type I callus, type II callus, somatic embryogenic callus and any culture which gives rise to somatic embryos or shoots. Alternatively the plant material could be derived from plant tissues such as leaves, stems, roots or flowers.

Preferably, the buffering agent used prevents or delays the rapid rise in pH of the culture medium in which the plant material is transformed or in which the transformed plant materials is being regenerated into a transgenic plant. More preferably the pH is maintained between pH 5.5–6.5.

Preferably the buffering agent is selected from the group consisting of 2-[N-morpholino] ethane sulfonic acid buffer (MES), N-[2-acetamido]-2-iminodiacetic acid buffer (ADA) and bis[2-hydroxyethyl]iminotris[hydroxymethyl]methane buffer (BIS-TRIS) or a solution containing ammonium and nitrate ions in a predetermined ratio. In the light of the teaching of this disclosure those skilled in the art will be able to identify other buffers suitable for use in the method.

Preferably the exogenous genetic material is introduced into plant cells by a plant transformation agent, most preferably *Agrobacterium tumefaciens*. In another preferred embodiment the exogenous genetic material may be introduced using a mechanical method such as microparticle bombardment. Other methods of introducing exogenous genetic material into plant material would be clear to those skilled in the art.

The genetic material may be DNA or RNA and may encode a gene or a fragment of a gene, or it may represent antisense nucleotide sequences of endogenous genes. Preferably the exogenous genetic material encodes a mRNA or protein that confers on the transgenic plant a property selected from the group comprising: increased alkaloid yield relative to the native alkaloid producing plant, increased herbicide resistance relative to the native alkaloid producing plant, increased soil acidity tolerance relative to the native alkaloid producing plant, increased disease resistance relative to the native alkaloid producing plant, increased insect resistance relative to the native alkaloid producing plant, increased growth rate relative to the native alkaloid producing plant, improved flowering properties relative to the native alkaloid producing plant, increased frost tolerance relative to the native alkaloid producing plant and altered alkaloid proportions relative to the native alkaloid producing plant. Most preferably the exogenous genetic material encodes a mRNA or protein that confers on the transgenic poppy the property of altered alkaloid proportions relative to the native alkaloid producing plant. When the exogenous genetic material encodes a mRNA or protein that confers on the transgenic poppy the property of herbicide resistance, preferably the herbicide resistance is Basta herbicide resistance, glyphosate resistance, bromoxynil resistance or sulfonylurea resistance.

Preferably the exogenous genetic material is comprised in a DNA construct based on the binary vector pPZP, most preferably pTAB101 with 35S 5':pat:35S 3'. In another preferred embodiment the binary vector is pBSF16. In a particularly preferred embodiment, the binary vector is pPOP5.

According to a fourth aspect the invention consists in a transgenic plant prepared by the method of any one of the preceding aspects.

Preferably the plant is an alkaloid producing poppy plant and even more preferably the plant is selected from the *Papaver* species or *Eschscholtzia* species. The most preferred species is *Papaver somniferum*.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

DESCRIPTION OF THE PREFERRED EMBODIMENT

The method comprises in part the use of conventional methods of plant transformation and regeneration of transgenic plants but in addition includes steps which improve the conventional methods by stabilising the pH of the medium by way of either preventing or delaying the rapid rise in pH of the culture medium or the plant material. In particularly advantageous variants of the methods of the present invention the pH is stabilised within the range of pH 5.5–6.5 during both transformation and regeneration of transgenic plants.

In most plant species studied, the introduction of recombinant DNA and the culture of seedling explants on standard tissue culture media is not accompanied by a large rise in pH, however, this hitherto unexpected phenomena has been identified in poppy cultures. It has been observed by the applicants that there is an unexpected and rapid rise in the pH of tissue culture media used to support the growth of *Papaver somniferum* tissues or cells. This phenomenon may also apply to other plants and this can be simply ascertained by those skilled in the art. This very rapid and substantial rise, for example, from pH 5.6 to pH>6.4 in the immediate area around a Type II callus in B5O medium within 30 minutes, rising ultimately to pH 8.7, has been identified as a major cause of poor growth and the difficulty in producing transgenic poppies.

The preferred medium for transformation and culturing of transgenic plants is 1 gD (also referred to as the Callusing Medium) buffered with MES. However, any method or medium modification which for preference results in the medium pH remaining within the range of pH 5.5–6.5 is suitable for the method described herein, including, addition of MES buffer (eg 10 mM), addition of BIS-TRIS buffer (eg 10 mM), addition of ADA (eg 10 mM), modifying the ammonium and nitrate ion amounts and ratio in the medium (such as for example $NO_3^-/NH_4$ of 1:3, total N of 30 mM).

In addition to helping control the medium pH during culture, the buffering agents may produce direct or indirect benefits to the process such as improving *Agrobacterium*-mediated gene transfer, type II callus formation or somatic embryo formation and development. A number of authors have indicated the significance of pH on T-DNA transfer by *Agrobacterium* (Holford et al, 1992; Fenning et al 1996 a.b; Li and Komatsuda. 1995).

Figure 1:
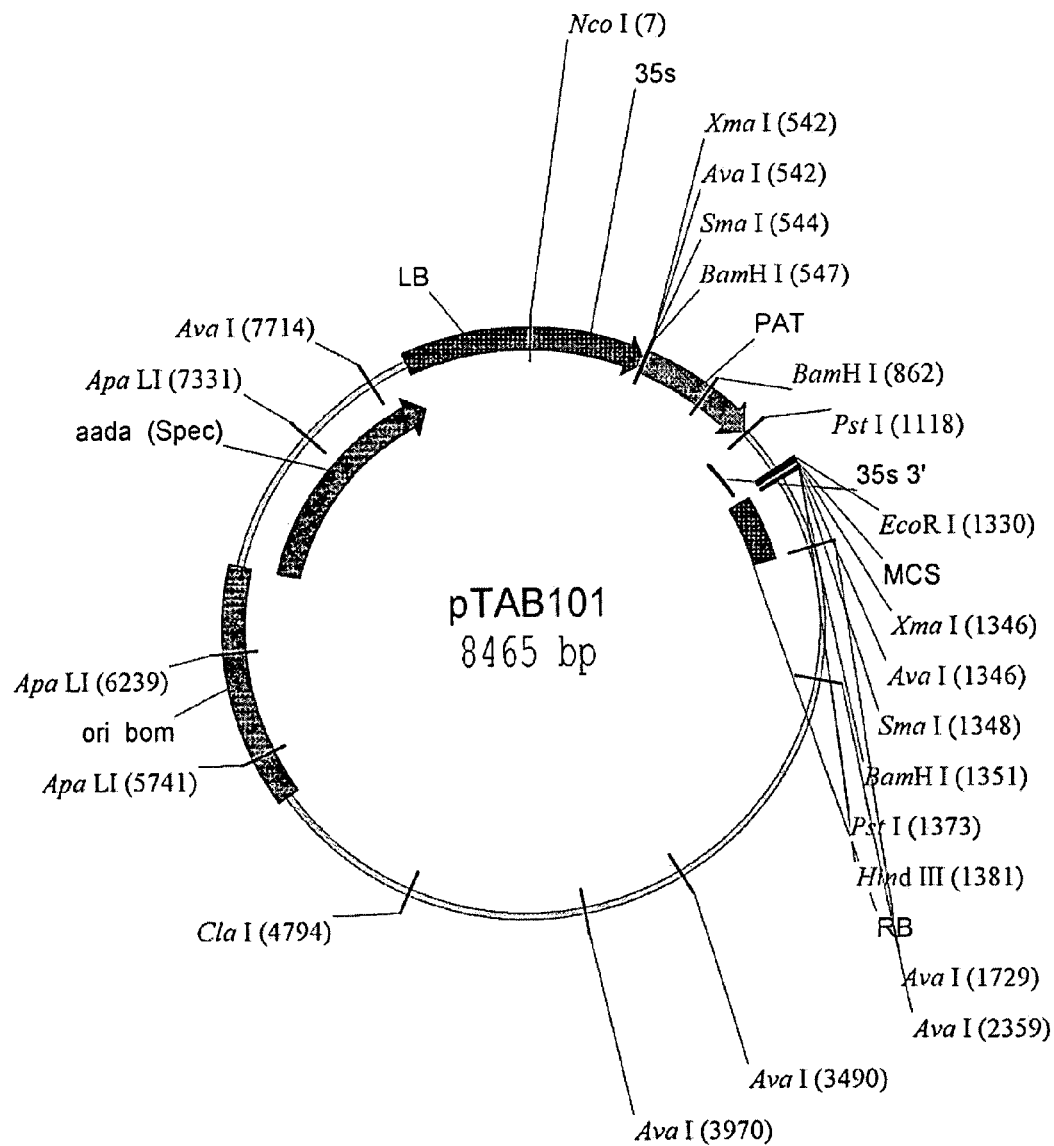
FIG. 1 Shows the plasmid pTAB101, which is a preferred vector for introducing exogenous genetic material in accordance with the present invention.

The preferred exogenous genetic material used in transformation is the binary vector TAB101 containing 35S 5':pat::35S 3' (see FIG. 1).

Figure 2:
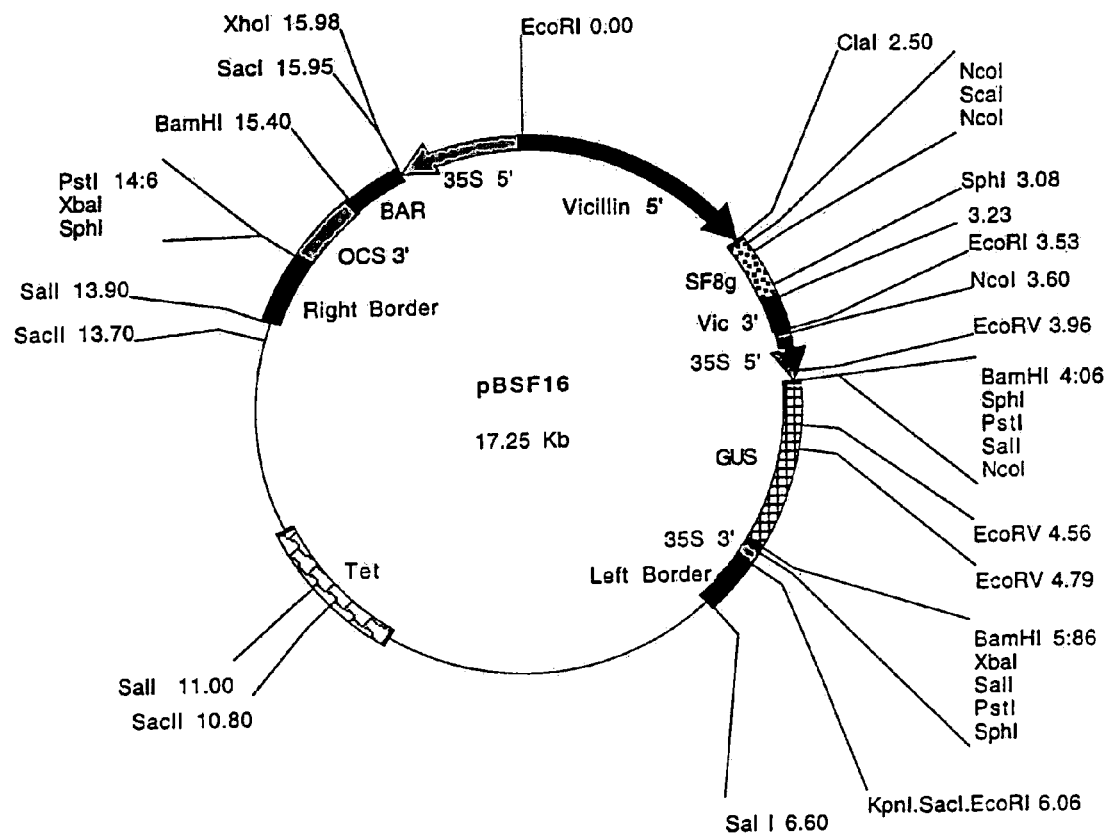
FIG. 2 Shows pBSF16, which is an alternative binary vector for introducing exogenous genetic material in accordance with the present invention.

Another preferred exogenous genetic material is the binary vector BSF16 (see FIG. 2.)

Figure 3:
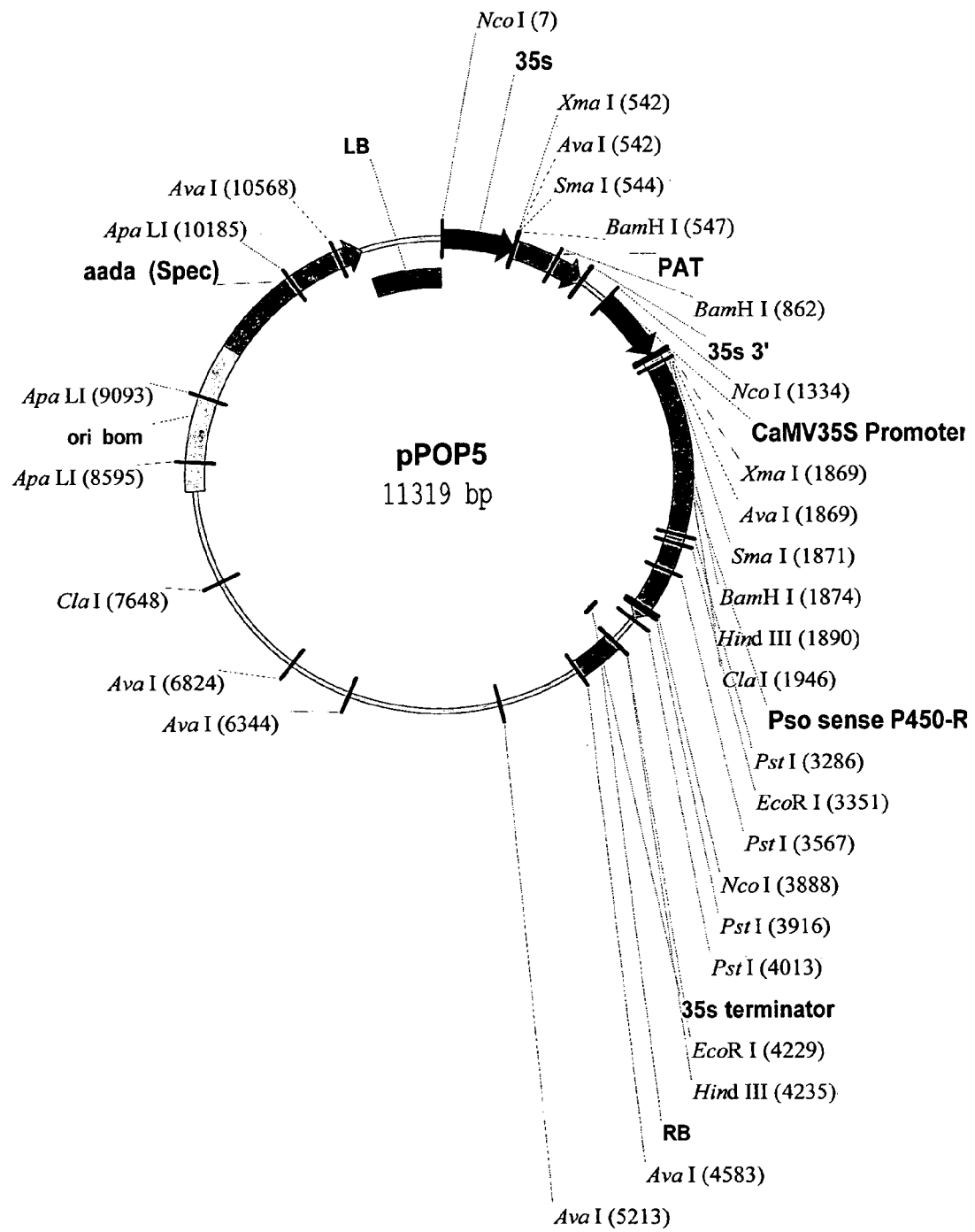
FIG. 3 Shows pPOP5, which is an alternative binary vector for introducing exogenous genetic material in accordance with the present invention.

A further preferred vector is pPOP5 (see FIG. 3) which has two genes in the T-DNA: the pat gene conferring Basta (or PPT) resistance; the *Papaver somniferum* P450 reductase gene which enables the cytochrome P450 reductase enzyme to accumulate to higher levels in the transgenic tissues; this enzyme donates electrons to reconstitute the cytochrome P450 complex which can be rate limiting for a number of cytochrome P450-dependent enzymes involved in morphine biosynthesis; the transgene is therefore expected to increase the biosynthesis of morphinan alkaloids.

The pat gene serves two purposes, as a selectable marker in vitro and as the herbicide resistance gene in the transgenic plant. As a selectable gene, it enables selection of transgenic cells in the culture using Basta herbicide or the active ingredient, glufosinate ammonium or phosphinothricin (also known as PPT). Those skilled in the art will know that alternative selectable genes could be employed such as those conferring hygromycin resistance, kanamycin resistance or spectinomycin resistance.

It will also be known to those skilled in the art that it is possible to introduce exogenous genetic material coding for more than one desirable property. For instance, the pBSF16 vector has three genes in the T-DNA: the bar gene conferring Basta (or PPT) resistance; the sunflower albumin gene, SF8g, which enables a novel sunflower seed albumin to accumulate in the seeds of the transgenic plant; the GUS reporter gene, which encodes β-glucuronidase and enables the detection of transgenic tissues.

EXAMPLES

Example 1

Plant Material

The genotypes of *Papaver somniferum* used were C 046-3-5. C 058, C 060, C 048-6-14-64 and D 233 (Norman) obtained from Tasmanian Alkaloids. Seeds are surface sterilised by washing for 30–60 seconds in 70% ethanol then in 1%(w/v) sodium hypochlorite solution plus 1–2 drops of autoclaved Tween 20 or Triton X for 20 minutes with agitation. Seeds are rinsed three to four times in sterile distilled water or until no smell of bleach remains and placed on 90×25 mm Petri dishes containing B5O medium (see below). Dishes are sealed with Micropore tape and are usually stored at 4° C. for 24 to 48 hours. Seeds are germinated at 24° C. in a 16 hour light-8 hour dark cycle. Hypocotyls are excised from seedlings after 7–8 days of culture and are cut into 3–6 mm explants (usually 1–3 explants per seedling) and used in transformation experiments.

Example 2

Tissue Culture Media and Conditions

B5O medium consists of B5 macronutrients, micronutrients, iron salts and vitamins (Gamborg et al. 1968), 20 g/L sucrose using 0.8% Sigma Agar as the gelling agent. pH is adjusted with 1M KOH to pH 5.6.

Callusing Medium (also referred to as 19D) is identical to B5O except that it includes 1 mg/L 2,4 dichloro phenoxy acetic acid (2,4-D).

19D may be buffered with the appropriate buffering agent selected from MES, BIS-TRIS, ADA or modified $NO_3/NH_4$+ionic ratios.

Medium #7 is 19D but modified in $NO_3^-/NH_4^+$ content to achieve a ratio of 1:3 with a total N of 30 mM.

Buffering agents are added prior to autoclaving.

All media is autoclaved at 121° C. for 20 minutes.

Suitable antibiotics, such as timentin, are added to all media after autoclaving and cooling to 55–65° C.

Explant and type I callus cultures are grown in Petri dishes sealed with Micropore tape at 24° C. Type II callus and somatic embryos are cultured at 18–21° C.

Example 3

Bacterial Strains and Binary Vectors

The disarmed *Agrobacterium tumefaciens* strains AGLO and AGL1 (Lazo et al., 1991) are used in transformation experiments. DNA constructs are based on the binary vector pPZP201 (Hajdukiewicz et al, 1994), e.g. pTAB101 (see FIG. 1) with 35S 5':pat:35S 3'. *Agrobacterium* strains are maintained in glycerol at −80° C. or on LB agar plates plus appropriate selection at 4° C. Fresh cultures are grown overnight at 28° C. in 10 mL MG broth (Garfinkle and Nester, 1980) without antibiotics. This *Agrobacterium* suspension is diluted to approximately $5 \times 10^8$ cells $mL^{-1}$ (OD600=0.25) for use in transformation experiments.

Example 4

Transformation and Embryogenesis

Hypocotyls are excised from seedlings and immediately inoculated by immersion in liquid *Agrobacterium* culture for $10^{-15}$ minutes. Explants are then transferred directly to 19D, with or without buffering agent, or medium #7. After four to five days co-cultivation explants are washed in sterile distilled water, until the water is clear of *Agrobacterium*, blotted on sterile filter paper and transferred to 1 gD, with or without buffering agent, or medium #7 containing 150 mg/L Timentin plus 10 mg/L PPT (phosphinothricin, the active ingredient of Basta herbicide). Timentin is included to control *Agrobacterium* overgrowth and it will be clear to those skilled in the field that suitable alternative antibiotics or agents may also be used. Explants are transferred to fresh 1 gD, with or without buffering agent, or medium #7, at three weekly intervals. They initially produce friable brownish type I callus and may subsequently form small regions of very white, compact embryogenic callus (type II) by about 7–8 weeks culture.

Type II callus is transferred to B5O containing 150 mg/L Timentin plus 10 mg/L PPT and cultures are transferred to fresh medium every three weeks. Meristemoid/embryo development usually occurs after one or two periods on B5O medium and are seen from about 14–16 weeks total culture time.

Plantlet development from embryos is slow and may require a further 3 months in tissue culture before shoot and root growth is sufficient to ensure successful transplantation to soil.

Example 5

Importance of pH Buffering

If the initial pH of the medium is 5.8 and buffering agent is omitted, the pH of poppy cultures rapidly rises to pH 8.0 or higher when the callus mass reaches about 1 cm diameter. Fresh agar-solidified B5-based medium adjusted to pH 5.6 rose to pH>6.4 in the immediate area around type II callus within 30 mins. The inclusion of chlorophenyl red in the medium was sometimes used to observe these localised increases in pH; the medium turns purple at pH6.4. The whole plate was pH>7 within 24 h. At the end of the culture period pH values were measured at 8.7. This rapid rise in pH results in very poor growth which is not compensated for by frequent changes of medium. The rapid rise was significantly delayed even by 2.5 mM MES, but 10 mM MES is preferred to adequately buffer the medium and support improved growth over the 3 week subculture period. As shown in Table 1, the use of MES buffer, especially when used throughout the entire transformation and culture process, resulted in a substantial increase in recovery of transgenic plants.

Figure 4:
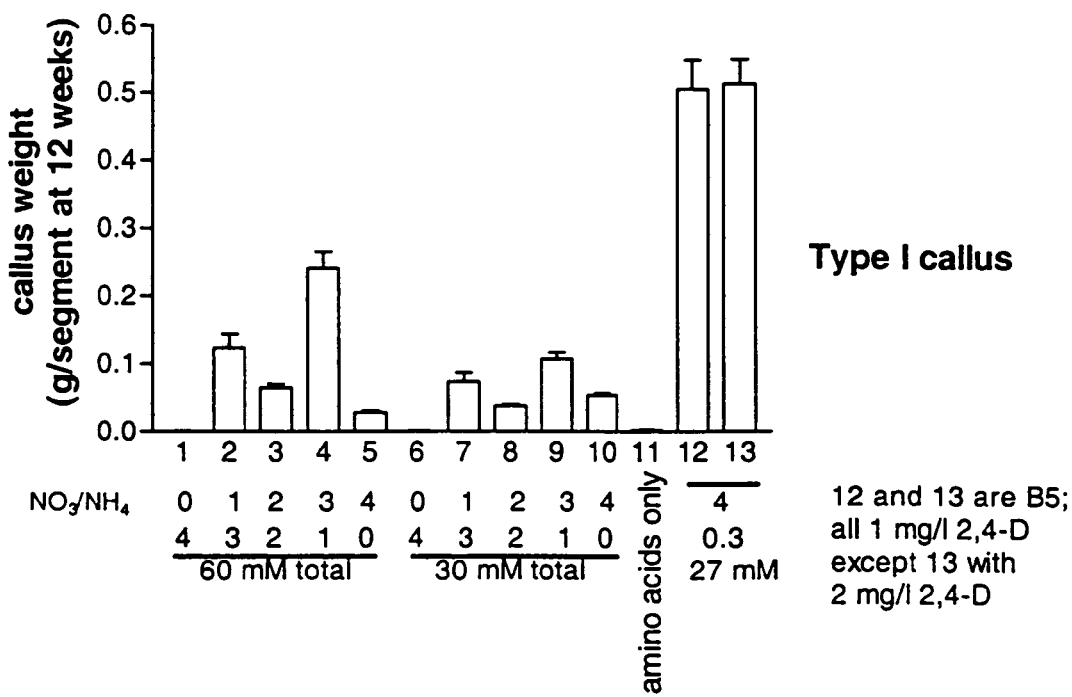
FIGS. 4A and 4B Show effects of various $NO_2^-$ $NH_4^-$ ratios in culture medium on type I and type II callus weight.
Figure 4:
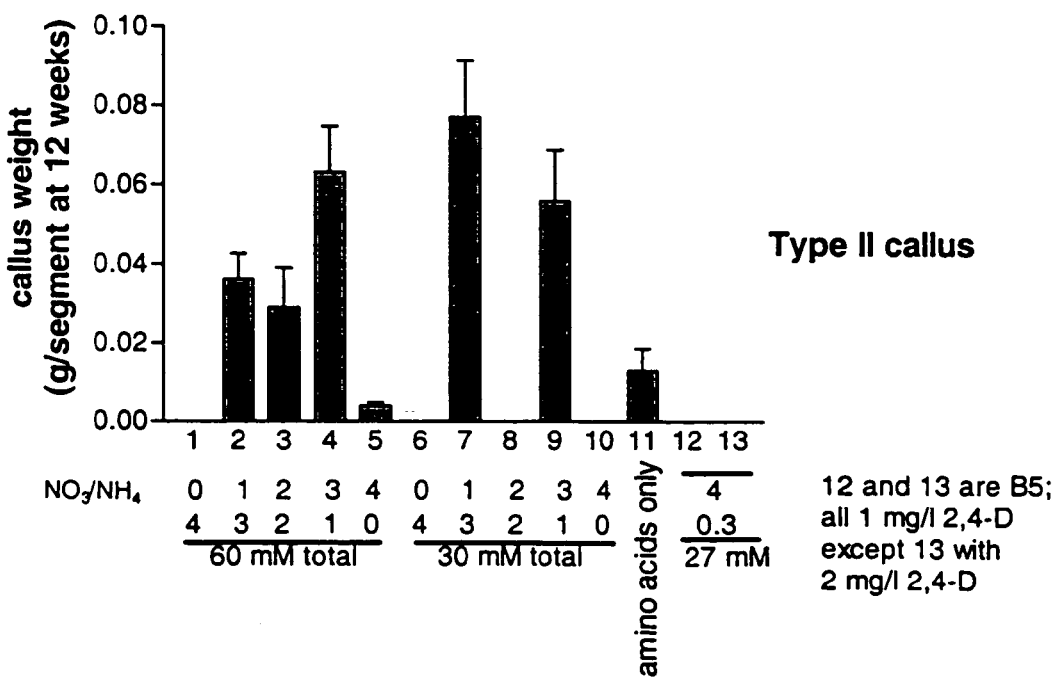

An experiment was set up to investigate any possible effects of total nitrogen levels, and the ratio of $NO_3^-:NH_4^-$. This experiment was prompted by literature implying the involvement of N interconversions in medium as a driving force for pH changes (Galvez and Clark, 1991; Nidez, 1994; Schmitz and Lörz, 1990; Smith and Krikorian, 1990). MES was not added to any of the media. After twelve weeks of culture, which included two transfers to fresh media, Type I and Type II calli were weighed. Results are presented in FIGS. 4A and 4B. There are obviously a number of media treatments that appear superior to our standard callusing medium 19D (medium #12 in FIGS. 4A and 4B), especially in terms of Type II (embryogenic) callus production. The failure of the standard medium to produce any type II callus in this experiment is attributable to the absence of MES. The medium #7 was chosen for further studies and as an alternative way to control pH changes in the medium.

The following experiments have focussed on the control of pH increases. The inbred cultivar C 048-6-14-64 was used throughout and the *Agrobacterium* used carried the pPOP5 binary vector with pat gene for selection (PPT as the selection agent).

Figure 5:
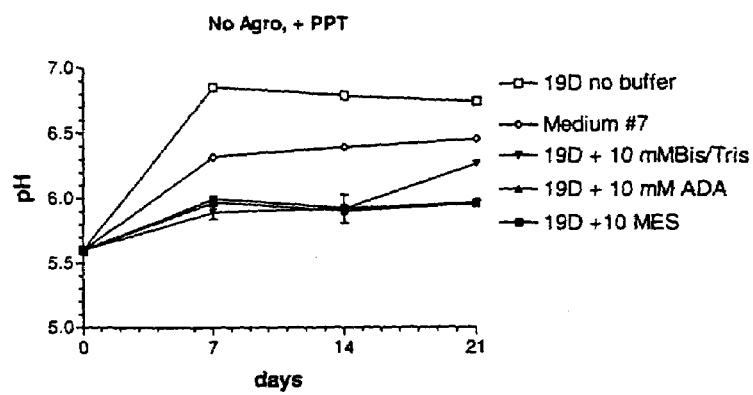
FIGS. 5A to 5C Show effects of various buffering agents on pH of the callus growth medium.
Figure 5:
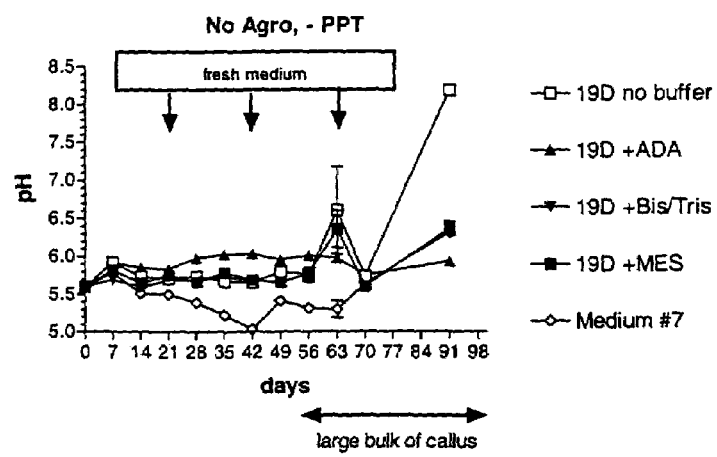
Figure 5:
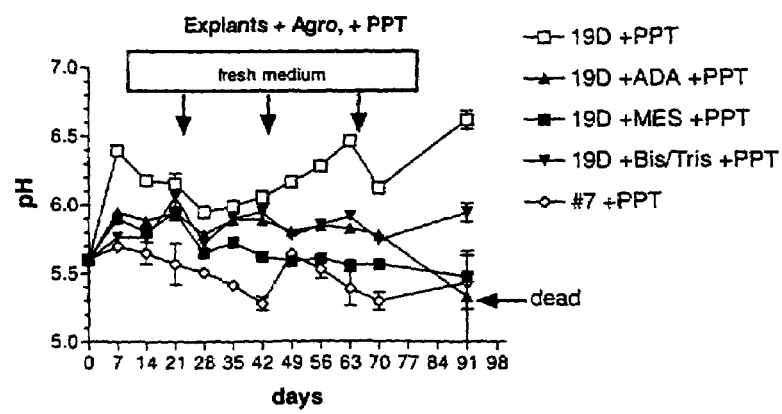

With *Agrobacterium* co-cultivation and PPT selection, the unbuffered medium (19D) did permit unacceptable rises in pH (FIG. 5C) and accumulation of black or brown pigments even though the amounts of tissue involved were very small. The pH was controlled by the addition of 10 mM of the buffers MES, ADA or Bis/Tris and the pigmentation was less severe. Unacceptable increases in medium pH were also controlled by a buffering strategy based on an alteration of the nitrate to ammonium ratio in medium #7 which has $NO_3^-:NH_4^+$ of 1:3 molar. The rise in pH was most extreme when explants were under PPT selection but had not been treated with *Agrobacterium* (FIG. 5A). After the first three weeks these cultures showed no growth as expected. Without PPT selection and without *Agrobacterium* cocultivation (FIG. 5B) the upward pressures on pH were not evident until the third culture period when the amount of tissue had increased.

Figure 6:
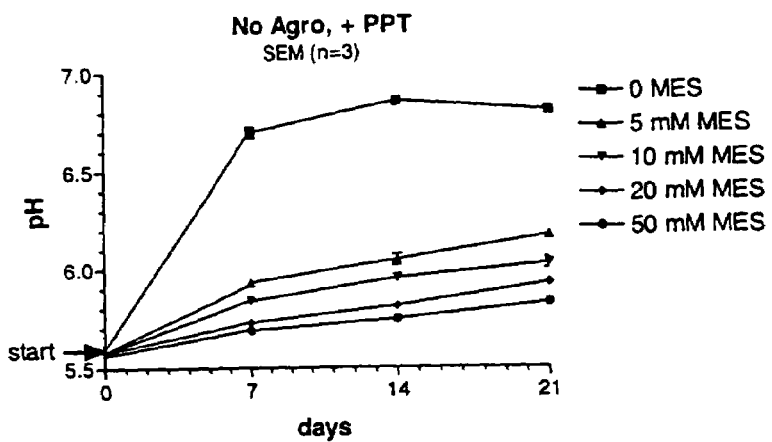
FIG. 6 Shows effects of various MES buffer concentrations on pH of the callus growth medium.
Figure 6:
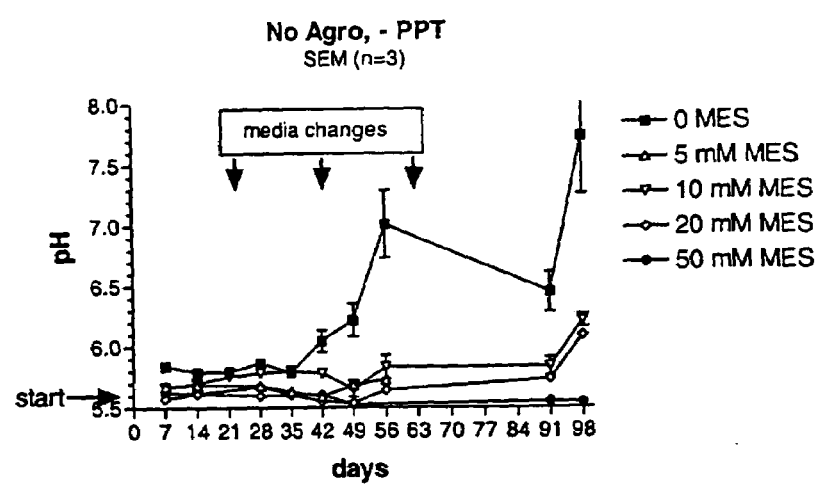
Figure 6:
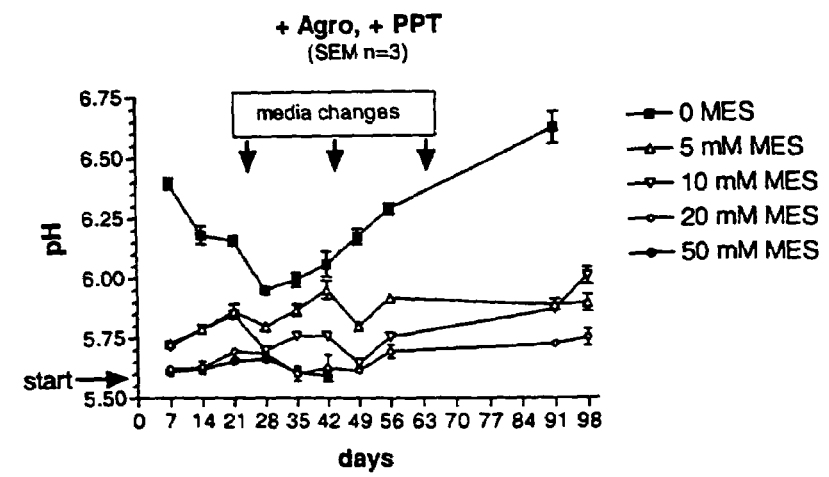

Adequate control of pH under the conditions used was achieved with 10 mM MES (FIGS. 6A, B, C). 50 mM MES in the absence of *Agrobacterium* and no PPT permitted healthy unpigmented growth. However, in the presence of *Agrobacterium* and with PPT selection, 20 and 50 mM MES were less effective gave no growth.

Pooled data over a number of experiments, using two poppy cultivars and a number of binary plasmids are shown in Table 1. These experiments are all under PPT selection.

TABLE 1

Pooled data from 8 experiments, using two poppy cultivars and a number of binary plasmids. These experiments are all under PPT selection.

| Medium for initiation of culture | Medium for later stages of the transformation | Number of explants | Number of putative transgenic plants | Number of independent transgenic events |
|---|---|---|---|---|
| 19D (no buffer) | 19D (no buffer) | 623 | 1 | 1 |
| 19D (no buffer) | 19D + 10 mM MES | 300 | 21 | 1 |

TABLE 1-continued

Pooled data from 8 experiments, using two poppy cultivars and a number of binary plasmids. These experiments are all under PPT selection.

| Medium for initiation of culture | Medium for later stages of the transformation | Number of explants | Number of putative transgenic plants | Number of independent transgenic events |
|---|---|---|---|---|
| 19D + 10 mM MES | 19D + 10 mM MES | 968 | ≧60 | ≧14 |

TABLE 2

One particular experiment as an example is shown in Table 2. Measurements were made at 9 weeks from initiation. All tissues were treated with Agrobacterium carrying pPOP5 and are under PPT selection.

| Medium | No. of explants (weighed in three pooled batches) | Type II callus mg per explant (mean ± SEM) | No. of transgenic shoots |
|---|---|---|---|
| 19D − MES | 21 | 14.4 ± 5.8 | 0 |
| 19D + MES | 24 | 32.7 ± 11.0 | 48 |
| 19D + BIS − TRIS | 30 | 19.2 ± 3.4 | no data |
| medium #7 | 15 | 29.4 ± 14 | no data |

Example 6

Figure 7:
FIG. 7 Shows results of a PAT (phosphinothriecin acetyl transferase) Assay. The arrow indicates the radioactive acetylated PPT band resulting from PAT enzyme activity. 1 and 9: A transgenic tobacco extract as a positive control. 2 and 10: A non-transgenic control poppy. 3–8: Various primary transgenic poppy plant extracts, from plants transformed with the pTAB101 binary vector.

We have confirmed the transgenic status of 23 poppy plants in soil, firstly by PAT assay (eg FIG. 7). These plants represent at least five independent transformation events. Two of the events are in the cultivar C 058 and three are in Norman. All plants in the glasshouse have flowered and seed has been collected.

Seed ($T_1$) from one line of C 058 and 4 lines of Norman have been sterilised and plated onto medium with and without 10 μg/ml PPT to check the viability of seed, stability of pat gene expression and segregation of the transgene. We have shown that the $T_1$ seed is viable and most progeny have inherited PPT resistance (Table 3).

TABLE 3

| Line | Total Seed | Abnormal Germination | Healthy Resistant | Susceptible | % R/R + S |
|---|---|---|---|---|---|
| Norman | 50 | 4 | 0 | 46 | 0% |
| Norm 48*1 | 48 | 6 | 19 | 9 | 68% |
| Norm 48*3 | 48 | 2 | 41 | 0 | 100% |
| Norm 48*4 | 49 | 1 | 45 | 0 | 100% |
| Norm 48*5 | 50 | 0 | 14 | 0 | 100% |

The failure to see susceptible segregants in three lines is not surprising, given that they have multiple inserts.

Seedlings were also germinated and grown without PPT selection and the segregation of PAT enzyme activity has been determined to date on one line (Table 4):

TABLE 4

| Line | Total Seedlings Tested | PAT + | PAT − | % PAT + |
|---|---|---|---|---|
| Norm 48*1 | 27 | 18 | 9 | 67% |

We have further confirmed the transgenic status of 9 plants representing at least 5 independent events by Southern blot analysis. Some lines appear to have only a single copy of the pat gene, whereas other lines show multiple inserts (Table 5).

TABLE 5

| Transgenic Line | Transgenic Event | PAT Transgene Copy Number (Estimate) |
|---|---|---|
| Norman 48*1 | a | 2–4 |
| Norman 48*3 and 4 | b | 12–20 |
| Norman 48*5 and *6 | c | 4 |
| C 058 42*1 | d | 1 |
| C 058 45*9 and *10 and *11 | e | 1 |

Figure 8:
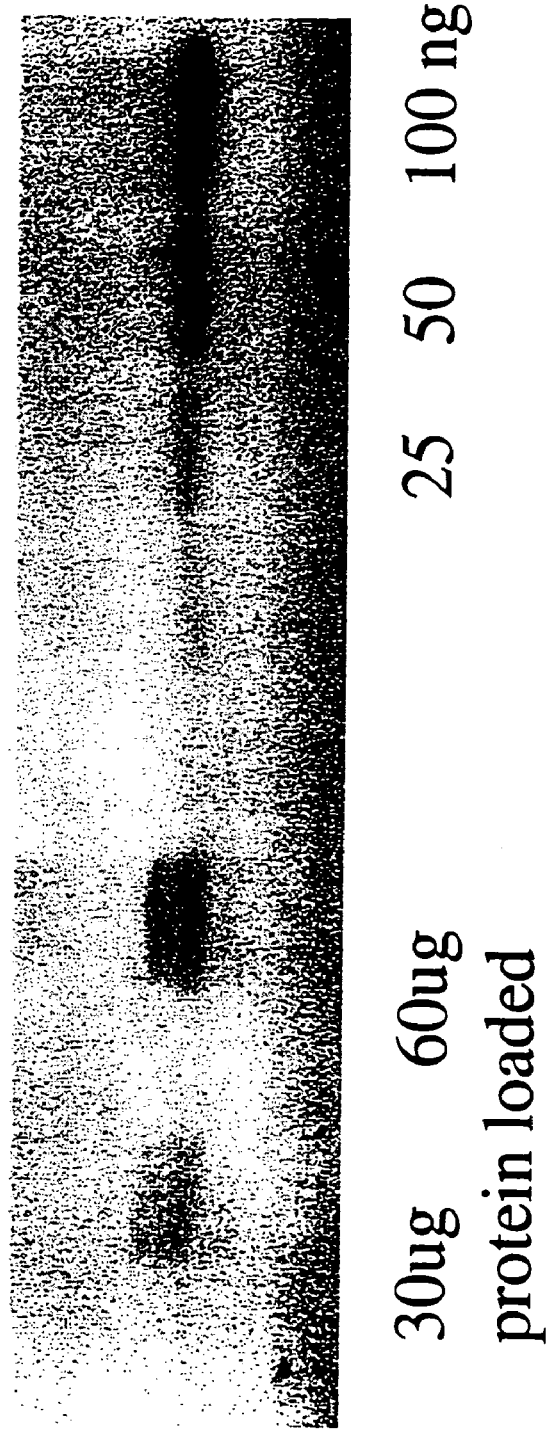
FIG. 8 Shows a western blot of seed from transgenic line 45-25, transformed with pBSF16. SSA standards are various amounts of sunflower seed albumin. C. is control non-transgenic seed extract. T, is transgenic seed extract. The signals results from specific binding of an antiserum to the sunflower seed albumin protein.

We have further confirmed the transgenic status of plants and their progeny by demonstrating the accumulation of sunflower seed albumin in the seeds of transgenics produced using the pBSF16 binary vector. This was demonstrated using antibodies specific for the sunflower albumin with Western blots of proteins prepared from control and transgenic seed (see FIG. 8).

The transgenic status of plants derived from pBSF16 was further demonstrated by incubating various tissues with a substrate for β-glucuronidase, enzyme encoded by the gus gene. In the presence of the substrate, X-glucuronide, leaves, stems, capsules and seeds all stained intensely blue, while the same tissues from non-transgenic controls did not develop any blue colour.

Although the invention has been described with reference to specific embodiments, modifications that are within the knowledge of those skilled in the art are also contemplated as being within the scope of the present invention.

REFERENCES

Fenning T M. Tymens S S. Brasier C M, Gartland J S, Gartland K M A, Ahuja M R, Boerjan W, and Neale D B. 1996. A strategy for the genetic manipulation of English elm. IN "Somatic cell genetics and molecular genetics of trees", pp. 105–112. Kluwer Academic Publishers. Dordrecht, Netherlands.

Fenning T M, Tymens S S, Gartland J S, Brasier C M, and Gartland K M A. 1996.

Transformation and regeneration of English elm using wild-type Agrobacterium tumefaciens. Plant Science (Limerick) 116:p 37–46.

Galvez, L., and R. B. Clark. 1991. Nitrate and Ammonium Uptake and Solution pH Changes for Al-Tolerant and Al-Sensitive Sorghum (Sorghum biocolor) Genotypes Grown with and Without Aluminium. Plant and Soil 134: 179–88.

Gamborg, O. L., Miller, R. A. and Ojima, K. (1968). Nutrient requirements of suspension cultures of soybean root cells. Exp. Cells Res. 50, 151–158.

Garfinkle, D. J. and Nester, E. W. (1980) Agrobacterium tumefaciens mutants affected in crown gall tumorigenesis and octopine catabolism. J. Bacteriol. 144, 732–743.

Hajdukiewicz, P., Svab, Z and Maliga, P. (1994). The small, versatile pPZP family of Agrobacterium binary vectors for plant transformation. Plant Mol. Biol. 25, 989–994.

Holford P, Hernandez N, and Newbury H J. 1992. Factors influencing the efficiency of T-DNA transfer during cocultivation of Antirrhinum majus with Agrobacterium tumefaciens. Plant Cell Reports 11: p 196–99.

Lazo, G. R., Stein, P. A. and Ludwig, R. A. (1991) A DNA transformation-competent *Arabidopsis* genomic library in Agrobacterium. *Bio/Technology,* 9, 963–967.

Li W B, and Komatsuda T. 1995. Impact of several factors related to inoculum, explants, compound and growth medium on tumorigenesis in vitro culture of soybean (*Glycine gracilis* and *G. Max*). *Soybean Genetics Newsletter* 22: p 93–98.

Niedz, R. P. 1994. Growth of embryogenic sweet orange callus on media varying in the ratio of nitrate to ammonium nitrogen. *Plant Cell Tissue and Organ Culture* 39: 1–5.

Schmitz; U., and H. Lorz. 1990. Nutrient Uptake in Suspension Cultures of Gramineae 2. Suspension Cultures of Rice (*Oryza Sativa* L). *Plant Science* 66: 95–111.

Smith, D. L., and A. D. Krikorian, 1990. Somatic Embryogenesis of Carrot in Hormone-Free Medium—External pH Control over Morphogenesis. *American Journal of Botany* 77: 1634-47.

What is claimed is:

1. A method of producing a transgenic alkaloid producing poppy plant of the *Papaver somniferum* species comprising the steps of:
   1) introducing an exogenous nucleic acid for conferring a selected property on the transgenic plant into transformable poppy plant material of the *Papaver somniferum* species in the presence of a buffering agent which stabilizes the pH of the plant material or culture medium within the range of pH 5.5 to pH 6.5;
   2) culturing the plant material in the presence of the buffering agent; and
   3) generating the transgenic plant from the plant material.

2. A method of transforming an alkaloid producing poppy plant of the *Papaver somniferum* species comprising the step of introducing an exogenous nucleic acid for conferring a selected property on the transgenic plant into transformable plant material of the poppy plant in the presence of a buffering agent which stabilizes the pH of the plant material or culture medium for culturing the plant medium within the range of pH 5.5 to pH 6.5.

3. A method of producing a transgenic alkaloid producing poppy plant of the *Papaver somniferum* species from transformable poppy plant material harbouring exogenous nucleic acid for conferring a selected property on the transgenic plant, comprising the steps of:
   1) culturing the plant material in culture medium in the presence of a buffering agent which stabilizes the pH of the plant material or culture medium for culturing the plant medium within the range of pH 5.5 to pH 6.5; and
   2) generating the transgenic plant from the plant material.

4. The method according to claim 2 wherein the transformable poppy plant material is selected from seeds, imbibed seeds and seedling parts of the plant.

5. The method according to claim 2 wherein the transformable poppy plant material is selected from the group consisting of seed explant, seedling explant, type I callus, type II callus, somatic embryogenic callus and plant tissues.

6. The method according to claim 2 wherein the buffering agent is selected from the group consisting of 2-[N-morpholino] ethane sulfonic acid buffer (MES), N-[2-acetamido]-2-iminodiacetic acid buffer (ADA) and bis[2-hydroxyethyl]iminotris-[ hydroxymethyl]methane buffer (BIS-TRIS), and a buffer having an ammonium and nitrate ions content in a predetermined ratio.

7. The method according to claim 2 wherein the exogenous nucleic acid is introduced into plant cells by a plant transformation agent.

8. The method according to claim 7 wherein the transformation agent is *Agrobacterium tumefaciens*.

9. The method according to claim 2 wherein the exogenous nucleic acid is introduced using a mechanical method.

10. The method according to claim 9 wherein the mechanical method is microparticle bombardment.

11. The method according to claim 2 wherein the exogenous nucleic acid encodes a mRNA or protein that confers on the transgenic plant a property selected from the group consisting of:
    increased alkaloid yield relative to the native alkaloid producing plant, increased herbicide resistance relative to the native alkaloid producing plant, increased soil acidity tolerance relative to the native alkaloid producing plant, increased disease resistance relative to the native alkaloid producing plant, increased insect resistance relative to the native alkaloid producing plant, increased growth rate relative to the native alkaloid producing plant, improved flowering properties relative to the native alkaloid producing plant, increased frost tolerance relative to the native alkaloid producing plant and altered alkaloid proportions relative to the native alkaloid producing plant.

12. The method according to claim 2 wherein the exogenous nucleic acid encodes a mRNA or protein that confers on the transgenic poppy the property of altered alkaloid proportions relative to the native alkaloid producing plant.

13. The method according to claim 2 wherein the exogenous nucleic acid encodes a mRNA or protein that confers on the transgenic poppy the property of herbicide resistance.

14. The method according to claim 13 wherein the herbicide resistance is selected from the group consisting of Basta herbicide resistance, glyphosate resistance, bromoxynil resistance and sulfonylurea resistance.

* * * * *